US011162126B2

(12) United States Patent
Cagnac et al.

(10) Patent No.: US 11,162,126 B2
(45) Date of Patent: Nov. 2, 2021

(54) METHOD FOR THE CULTURE OF UNICELLULAR RED ALGAE

(71) Applicant: FERMENTALG, Libourne (FR)

(72) Inventors: Olivier Cagnac, Libourne (FR); Lannig Richard, Begles (FR); Julie Labro, Bordeaux (FR)

(73) Assignee: FERMENTALG, Libourne (FR)

( * ) Notice: Subject to any disclaimer, the term of this patent is extended or adjusted under 35 U.S.C. 154(b) by 0 days.

(21) Appl. No.: 15/762,806

(22) PCT Filed: Sep. 22, 2016

(86) PCT No.: PCT/EP2016/072582
§ 371 (c)(1),
(2) Date: Mar. 23, 2018

(87) PCT Pub. No.: WO2017/050917
PCT Pub. Date: Mar. 30, 2017

(65) Prior Publication Data
US 2018/0274002 A1    Sep. 27, 2018

(30) Foreign Application Priority Data
Sep. 25, 2015 (FR) ...................................... 1559072

(51) Int. Cl.
| | | |
|---|---|---|
| *A61K 38/00* | (2006.01) | |
| *C12P 21/00* | (2006.01) | |
| *A23L 2/58* | (2006.01) | |
| *C12N 1/12* | (2006.01) | |
| *A23L 5/46* | (2016.01) | |
| *C12P 17/16* | (2006.01) | |
| *C12P 23/00* | (2006.01) | |
| *A23L 5/43* | (2016.01) | |
| *C07K 14/405* | (2006.01) | |
| *C07K 1/14* | (2006.01) | |

(52) U.S. Cl.
CPC ................. *C12P 21/00* (2013.01); *A23L 2/58* (2013.01); *A23L 5/43* (2016.08); *A23L 5/46* (2016.08); *C07K 1/145* (2013.01); *C07K 14/405* (2013.01); *C12N 1/12* (2013.01); *C12P 17/165* (2013.01); *C12P 23/00* (2013.01)

(58) Field of Classification Search
None
See application file for complete search history.

(56) References Cited

U.S. PATENT DOCUMENTS

| | | | |
|---|---|---|---|
| 9,932,554 B2* | 4/2018 | Im ........................... | A01G 33/00 |
| 2013/0171702 A1 | 7/2013 | Calleja | |
| 2014/0199739 A1 | 7/2014 | Calleja et al. | |
| 2016/0046899 A1 | 2/2016 | Garnier et al. | |
| 2017/0253851 A1 | 9/2017 | Calleja et al. | |
| 2018/0271119 A1 | 9/2018 | Cagnac | |

FOREIGN PATENT DOCUMENTS

| | | |
|---|---|---|
| EP | 2730647 A1 | 5/2014 |
| FR | 2789399 A1 | 8/2000 |
| FR | 3041653 A1 | 3/2017 |
| WO | WO 2011/035166 A1 | 3/2011 |
| WO | WO 2012/035262 A1 | 3/2012 |
| WO | WO 2012/175866 A1 | 12/2012 |
| WO | WO 2014/074769 A2 | 5/2014 |
| WO | WO 2014/174182 A1 | 10/2014 |
| WO | WO 2016/030629 A1 | 3/2016 |
| WO | WO 2016/099261 A1 | 6/2016 |

OTHER PUBLICATIONS

Ternes (Metabolic Evolution in G. Sulphuraria, pp. 1-141, 2009).*
Barbier et al., "Comparative Genomics of Two Closely Related Unicellular Thermo-Acidophilic Red Algae, *Galdieria sulphuraria* and *Cyanidioschyzon merolae*, Reveals the Molecular Basis of the Metabolic Flexibility of *Galdieria sulphuraria*...," Plant Physiology, vol. 137, Feb. 2005, pp. 460-474.
Bumbak et al., "Best Practices in Heterotrophic High-Cell-Density Microalgal Processes: Achievements, Potential and Possible Limitations," Appl Microbiol Biotechnol, vol. 91, 2011 (published online May 13, 2011), pp. 31-46.
Chen et al., "High Cell Density Mixotrophic Culture of Spirulina platensis on Glucose for Phycocyanin Production Using a Fed-Batch System," Enzyme and Microbiol Technology, vol. 20, 1997, pp. 221-224.
DIC Lifetec Co., Ltd., "Linablue® Natural Blue Colorant Derived from DIC Spirulina," retrieved from URL:http://www.dlt-spl.co.jp/business/en/spirulina/linablue.html, 2012, pp. 1-4.
Eisele et al., "Studies on C-Phycocyanin from Cyanidium caldarium, a Eukaryote at the Extremes of Habitat," Biochimica et Biophysica Acta, vol. 1456, 2000, pp. 99-107.
Graverholt et al., "Heterotrophic High-Cell-Density Fed-Batch and Continuous-Flow Cultures of Galdieria sulphuraria and Production of Phycocyanin," Appl Microbiol Biotechnol, vol. 77, 2007 (published online Sep. 5, 2007), pp. 69-75.
Gross et al., "Heterotrophic Growth of Two Strains of the Acido-Thermophilic Red Alga *Galdieria sulphuraria*," Plant Cell Physiol., vol. 36, No. 4, 1995, pp. 633-638.
Henkanatte-Gedera et al., "Algal-Based, Single-Step Treatment of Urban Wastewaters," Bioresource Technology, vol. 189, 2015 (published online Apr. 6, 2015), pp. 273-278.

(Continued)

*Primary Examiner* — Hope A Robinson
(74) *Attorney, Agent, or Firm* — Birch, Stewart, Kolasch & Birch, LLP

(57) ABSTRACT

The invention relates to the field of alga culture, particularly the culture of unicellular red algae (URA). In particular, the invention relates to a method for the culture of unicellular red algae, characterized in that the specific culture conditions, in terms of lighting and nutrients, allow the production of a protein-rich biomass that can contain an increased amount of URA and produce, in addition to pigments, particularly phycocyanin and carotenoids: β-carotene and zeaxanthin. The invention also relates to the biomass that can be produced using the method of the invention, to the uses of the biomass and to products that can contain said biomass.

20 Claims, 4 Drawing Sheets

(56) References Cited

OTHER PUBLICATIONS

Jaouen et al., "Clarification and Concentration with Membrane Technology of a Phycocyanin Solution Extracted from Spirulina platensis," Biotechnology Techniques, vol. 13, 1999, pp. 877-881.
Kao et al., "Physical-Chemical Properties of C-Phycocyanin Isolated from an Acido-Thermophilic Eukaryote, Cyanidium caldarium," Biochem. J., vol. 147, 1975, pp. 63-70.
Moon et al., "Isolation and Characterization of Thermostable Phycocyanin from Galdieria sulphuraria," Korean J. Chem. Eng., vol. 31, No. 3, 2014, pp. 490-495.
Nichols et al., "Action Spectra Studies of Phycocyanin Formation in a Mutant of Cyanidium caldarium," Botanical Gazette, Dec. 1962, pp. 85-93.
Nichols et al., "Studies on Phycobilin Formation with Mutants of Cyanidium caldarium," Nature, vol. 188, Dec. 3, 1960, pp. 870-872.
Patrickios et al., "Polypeptide Amino Acid Composition and Isoelectric Point," Analytical Biochemistry, vol. 231, 1995, pp. 82-91 (11 pages total).
Rahman et al., "Thermostable Phycocyanin from the Red Microalga *Cyanidioschyzon merolae*, a New Natural Blue Food Colorant," J Appl Phycol, Nov. 21, 2016, 7 pages.
Rellán et al., "First Detection of Anatoxin-a in Human and Animal Dietary Supplements Containing Cyanobacteria," Food and Chemical Toxicology, vol. 47, 2009, pp. 2189-2195.
Schmidt et al., "Heterotrophic High Cell-Density Fed-Batch Cultures of the Phycocyanin-Producing Red Alga *Galdieria sulphuraria*," Biotechnology and Bioengineering, vol. 90, No. 1, Apr. 5, 2005 (published online Feb. 18, 2005), pp. 77-84.
Schulze et al., "Light Emitting Diodes (LEDs) Applied to Microalgal Production," Trends in Biotechnology, vol. 32, No. 8, Aug. 2014, pp. 422-430.
Sloth et al., "Accumulation of Phycocyanin in Heterotrophic and Mixotrophic Cultures of the Acidophilic Red Alga *Galdieria sulphuraria*," Enzyme and Microbial Technology, vol. 38, 2006, pp. 168-175.
Stadnichuk et al., "Inhibition by Glucose of Chlorophyll α and Phycocyanobilin Biosynthesis in the Unicellular Red Alga *Galdieria partita* at the stage of Coproporphyrinogen III Formation," Plant Science, vol. 136, 1998, pp. 11-23.
Steinmüller et al., "Photo- and Metabolite Regulation of the Synthesis of Ribulose Bisphosphate Carboxylase/Oxygenase and the Phycobiliproteins in the Alga Cyanidium caldarium," Plant Physiol., vol. 76, 1984, pp. 935-939.
Tischendorf et al., "Ultrastructure and Enzyme Complement of Proplastids from Heterotrophically Grown Cells of the Red Alga *Galdieria sulphuraria*," European Journal of Phycology, vol. 42, No. 3, pp. 243-251 (10 pages total).

\* cited by examiner

METHOD FOR THE CULTURE OF UNICELLULAR RED ALGAE

FIELD OF THE INVENTION

The present invention relates to the field of culturing unicellular red algae (URA).

The invention particularly relates to a method for culturing URA, characterized in that the particular culture conditions in terms of illumination and nutrients make it possible to obtain biomass consisting of URA in higher amounts than that which can be obtained under traditional culture conditions, said biomass which can have at least a high amount of phycobiliproteins, particularly of phycocyanin, and in addition a high amount of antioxidants. The invention also relates to the biomass obtainable by the method according to the invention, to the uses of said biomass and to the products which can include said biomass.

STATE OF THE ART

Certain unicellular red algae (URA) can be useful as an additional food source because they can be a source of proteins, particularly phycobiliproteins, of fibre, of lipids and of antioxidants, particularly carotenoids. They can be used in the native state, advantageously dried, but also processed, for example reduced to flour.

They can be used in human or animal diets, as a nutritional supplement, or can be incorporated in small amounts into food.

The red algae, or rhodophytes (division Rhodophyta), are a large taxon of mostly marine, mostly multicellular algae. They are characterized by a pigmentary composition with only one type of chlorophyll, chlorophyll "a", carotenoids and characteristic pigments, the phycobiliproteins.

Among the rhodophytes there is a subdivision, the Cyanidiophytina, URA that live in acidic hot springs.

The subdivision Cyanidiophytina contains the class Cyanidiophyceae, which itself contains the order Cyanidiales, itself including the families Cyanidiaceae and Galdieriaceae, themselves subdivided into the genera *Cyanidioschyzon*, *Cyanidium* and *Galdieria*, whose members include the species *Cyanidioschyzon merolae* 10D, *Cyanidioschyzon merolae* DBV201, *Cyanidium caldarium*, *Cyanidium daedalum*, *Cyanidium maximum*, *Cyanidium partitum*, *Cyanidium rum pens*, *Galdieria daedala*, *Galdieria maxima*, *Galdieria partita* and *Galdieria sulphuraria*.

The phycobiliproteins are water-soluble pigments found in the phycobilisome, a photosynthetic complex present in cyanobacteria and certain microalgae. There are four types of phycobiliproteins: phycocyanin, phycoerythrin, allophycocyanin. Phycocyanin has an absorption peak between 610 nm and 655 nm, phycoerythrin has an absorption peak between 400 nm and 600 nm, phycoerythrocyanin has absorption peaks at about 450, 525 and 570 nm, and allophycocyanin has an absorption peak essentially centred at 650 nm.

Worldwide phycobiliprotein production is essentially obtained by culturing *spirulina* in open raceway ponds and represents about 15,000 tons per year.

Phycocyanin extracted from *spirulina* is also sold as a food supplement in liquid form, or in powder form for use as blue pigment in food. Phycocyanin is the only natural blue pigment approved by the US-FDA (FR Doc No: 2013-19550).

*Spirulina* cultures are mainly grown in the open air in hot geographical regions, the optimal culture temperature being 37° C. These cultures are thus dependant on seasonal fluctuations (temperature, light). *Spirulina* has the disadvantage of low productivity of biomass (g of dry biomass/L/h) and/or of phycocyanin (g of phycocyanin/L/h), which does not allow the transition to fermenter culture necessary to the industrialization of phycocyanin production.

Moreover, these cultures are also sensitive to contamination by forms of cyanobacteria, similar to *spirulina*, known to produce toxins such as microcystins [Rellan, S, et al. Food and Chemical Toxicology 47 (2009) 2189-2195]. Microcystins can cause intestinal problems, and long-term exposure to these toxins can cause liver cancer. In addition, certain strains of *spirulina*, for instance *Arthrospira platensis*, are themselves producers of toxins [Rellan, S, et al., op. cit.].

Tests of axenic *spirulina* cultures in closed bioreactors have been reported in the literature using a strain of *Arthrospira platensis* [Chen, Feng, and Yiming Zhang; Enzyme and Microbial Technology 20, no. 3 (Feb. 15, 1997): 221-24]. However, to the Applicant's knowledge, no industrial-scale production of *spirulina* in bioreactors has been reported.

It is therefore understood that in addition to low biomass and/or phycocyanin productivity, how to guarantee the health safety of productions intended for direct use of *spirulina* biomass in food or animal feed is not obvious and requires extremely precise quality control.

URA are known to produce phycocyanins, and the effect of light on the cultivation of URA and the pigment compositions thereof has been the subject of numerous laboratory studies [Sloth J K et al., Enzyme and Microbial Technology, Vol. 28, no. 1-2, January 2006, 168-175; Graverholt O S et al., Applied Microbiology and Biotechnology, Vol. 77, no. 1, 5 Sep. 2007, 69-75]. Nichols K et al. [Botanical Gazette, Vol. 124, no. 2, 1 Dec. 1962, 85-93] studied the cell photoreceptors believed to be associated with phycocyanin synthesis in mutant URA, while varying the wavelengths used to illuminate the cultures. Steinmuler K et al. [Plant Physiology, Vol. 76, no. 4, 1 Dec. 1984, 935-939] studied the culture of URA under mixotrophic conditions and noted that adding glucose could inhibit the synthesis of phycobiliproteins.

There is a need, therefore, for a new source of phycobiliproteins, particularly of phycocyanin, the culture methods of which would make it possible to overcome the known disadvantages of *spirulina* cultures.

It would be advantageous to have a method for culturing URA which would produce biomass of said algae having a higher amount of algae in relation to the amounts generally obtained by the methods for culturing said algae of the prior art and, moreover, which is to advantageously rich in metabolites of interest, particularly in phycobiliproteins, particularly in phycocyanin, and/or in antioxidants such as carotenoids, for example.

The present invention aims to provide such a method for culturing unicellular red algae (URA) enriched in phycobiliproteins and carotenoids.

DISCLOSURE OF THE INVENTION

The present invention relates to a method for culturing unicellular red algae (URA) of the class Cyanidiophyceae, in a medium comprising at least one carbon source, said method comprising at least one illumination step in the form of radiation having a narrow wavelength spectrum between 400 and 550 nm.

The invention also relates to biomass obtainable by the method according to the invention which has a phycobiliprotein (phycocyanin and allophycocyanin) content between 29 and 250 mg/g of dry weight and advantageously a URA density between 20 and 200 g/L of dry weight, preferentially between 90 and 150 g/L of dry weight.

The invention also relates to the use of the biomass according to the invention for preparing phycocyanin and/or carotenoids.

The invention also relates to a phycocyanin obtainable from the biomass according to the invention.

The invention also relates to the use of the biomass according to the invention or the phycocyanin according to the invention for food or animal feed, cosmetics and/or as dye.

The invention also relates to a product comprising at least the biomass or a phycocyanin according to the invention.

DETAILED DESCRIPTION OF THE INVENTION

Hereinafter in the present text, out of convenience and subject to further clarification, the use of "URA" must be understood as meaning "rhodophytes, of the subdivision Cyanidiophytina, of the class Cyanidiophyceae of the order Cyanidiales of the family Cyanidiaceae or Galdieriaceae, of the genus *Cyanidioschyzon, Cyanidium* or *Galdieria*, of the species *Cyanidioschyzon merolae* 10D, *Cyanidioschyzon merolae* DBV201, *Cyanidium caidarium, Cyanidium daedalum, Cyanidium maximum, Cyanidium partitum, Cyanidium rum pens, Galdieria daedala, Galdieria maxima, Galdieria partita* or *Galdieria sulphuraria*".

Similarly, use of the term "Cyanidiophyceae" must be understood, subject to further clarification, as meaning "Cyanidiophyceae, of the order Cyanidiales Cyanidiales, of the family Cyanidiaceae or Galdieriaceae, of the genus *Cyanidioschyzon, Cyanidium* or *Galdieria*, of the species *Cyanidioschyzon merolae* 10D, *Cyanidioschyzon merolae* DBV201, *Cyanidium caidarium, Cyanidium daedalum, Cyanidium maximum, Cyanidium partitum, Cyanidium rumpens, Galdieria daedala, Galdieria maxima, Galdieria partita* or *Galdieria sulphuraria*"; use of the term "Cyanidiales" must be understood, subject to further clarification, as meaning "Cyanidiales, of the family Cyanidiaceae or Galdieriaceae, of the genus *Cyanidioschyzon, Cyanidium* or *Galdieria*, of the species *Cyanidioschyzon merolae* 10D, *Cyanidioschyzon merolae* DBV201, *Cyanidium caidarium, Cyanidium daedalum, Cyanidium maximum, Cyanidium partitum, Cyanidium rum pens, Galdieria daedala, Galdieria maxima, Galdieria partita* or *Galdieria sulphuraria*"; use of the expression "Cyanidiaceae or Galdieriaceae" must be understood, subject to further clarification, as meaning "Cyanidiaceae or Galdieriaceae, of the genus *Cyanidioschyzon, Cyanidium* or *Galdieria*, of the species *Cyanidioschyzon merolae* 10D, *Cyanidioschyzon merolae* DBV201, *Cyanidium caidarium, Cyanidium daedalum, Cyanidium maximum, Cyanidium partitum, Cyanidium rumpens, Galdieria daedala, Galdieria maxima, Galdieria partita* or *Galdieria sulphuraria*"; use of the expression "*Cyanidioschyzon, Cyanidium* or *Galdieria*", must be understood, subject to further clarification, as meaning "*Cyanidioschyzon, Cyanidium* or *Galdieria*, of the species *Cyanidioschyzon merolae* 10D, *Cyanidioschyzon merolae* DBV201, *Cyanidium caidarium, Cyanidium daedalum, Cyanidium maximum, Cyanidium partitum, Cyanidium rumpens, Galdieria daedala, Galdieria maxima, Galdieria partita* or *Galdieria sulphuraria*".

It should also be noted that, such as they may be used in the description and the claims, the singular forms "a" and "an" include their plurals, unless the context clearly states otherwise.

Certain URA are mixotrophs, capable of both heterotrophy (consumption of organic carbon substrate provided by the culture medium) and autotrophy (use of light to capture $CO_2$ via photosynthesis). Mixotrophy is also called photoheterotrophy. The concept of mixotrophy extends to the use of light not only for photosynthesis but also as a light signal that can induce a metabolic response, for example the synthesis of pigments.

Heterotroph-dominant mixotrophy makes it possible to produce molecules of algal origin by coupling the advantages of both autotrophy and heterotrophy. It consists in introducing a light component of low intensity and short duration, with a culture medium which can contain one or more organic sources of carbon. As in heterotrophy, URA consume an organic substrate, which makes it possible to achieve high biomass productivity (expressed in grams of dry biomass/L/h) and/or biomass concentration (expressed in grams of dry biomass/L), the chloroplast and the other light-sensitive cell structures thus being activated.

These light-energy receptors can be specific organelles or structures within the cell, such as the chloroplast, the stigma, the chronoplast, the chromoplast or the phycobilisome, or can be individual molecules capable of responding to light and of producing a cellular response, such as the rhodopsins, the phytochromes, the cryptochromes or the aureochromes.

These photoreceptors enable the cell to have higher productivity and to synthesize all the molecules that can be metabolized by a URA. The molecules of interest produced by said URA are of major industrial interest particularly in the fields of nutrition, cosmetics, green chemistry and energy.

These molecules of interest are varied and include, for example, carbohydrates, proteins, amino acids, advantageously essential amino acids and pigments, particularly photosynthetic pigments, the principal ones being chlorophylls, carotenoids and phycobiliproteins.

The term carotenoid includes the carotenes ($\alpha$, $\beta$, $\varepsilon$, $\gamma$, $\delta$ and $\zeta$-carotene, lycopene and phytoene) and the xanthophylls (astaxanthin, antheraxanthin, citranaxanthin, cryptoxanthin, canthaxanthin, diadinoxanthin, diatoxanthin, flavoxanthin, fucoxanthin, lutein, neoxanthin, rhodoxanthin, rubixanthin, siphonaxanthin, violaxanthin, zeaxanthin). The carotenoids are liposoluble pigments, generally orange and yellow. They are synthesized by all algae, all green plants and by many fungi and bacteria (including cyanobacteria). They are absorbed by animals and humans through their food. The carotenoids have two main absorption peaks situated around 440 and 475 nm.

The carotenoids play an important role in nutrition and health, because several are provitamins A, and some also have anti-cancer and antioxidant activities. Moreover, they stimulate antibody synthesis. Some are widely used in the agri-food industry for their dye properties, and also in the cosmetics and pharmaceuticals industries for their antioxidant properties and their photoprotective capacity.

Certain carotenoids, such as lutein, zeaxanthin and astaxanthin, are of great interest, the latter particularly for its high antioxidant capacity.

The Applicant has shown, surprisingly and after extensive research, that culturing URA in a medium which can comprise at least one carbon source and one phosphorus source, and which can further comprise at least one illumination step, advantageously illumination by light having a narrow spectrum centred over a given wavelength, particularly a spectrum centred at 455 nm, can make it possible to obtain biomass in which the amount of URA can be substantially increased in relation to the cultures typically produced and which, moreover, can contain a potentially higher amount of molecules of interest, particularly phycocyanin, allophycocyanin, zeaxanthin and β-carotenes, than that which can be obtained in the cultures of the prior art.

The URA within the meaning of the invention are extremophilic organisms capable of tolerating very acidic pH (0.05-5) and very high temperatures (25-56° C.). These organisms are often found close to volcanos and thermal springs. Generally, these mixotrophic organisms are capable of using a large number of carbon metabolites (glucose, glycerol, pentose, etc.) [Wolfgang Gross and Claus Schnarrenberger. "Heterotrophic Growth of Two Strains of the Acido-Thermophilic Red Alga *Galdieria sulphuraria*." Plant and Cell Physiology 36, no. 4 (Jun. 1, 1995): 633-38].

Another advantage of the method developed by the Applicant is that it can be performed in a bioreactor and, moreover, advantageously on an industrial scale.

To the Applicant's knowledge, no industrial production (in a bioreactor) of URA under autotrophic, mixotrophic or heterotrophic conditions is known.

In particular, the Applicant has shown that culturing URA, within the meaning of the invention, using a culture medium comprising at least one carbon source and at least one assimilable source of phosphorus, said method comprising at least one illumination step, can make it possible to obtain a biomass productivity and/or a biomass concentration which is substantially increased in relation to the cultures typically produced, biomass which in addition can be rich in phycocyanin and/or in carotenoids.

By "rich in phycocyanin and/or in carotenoids" is meant in the present text that the concentration of phycobiliproteins and/or of carotenoids in the biomass that can be produced after culture under the conditions according to the invention is higher than the concentration of phycobiliproteins and/or of carotenoids that can be produced by biomass of the same algae obtained after culture under the conditions of the prior art.

A significant advantage of fermenter culture of Cyanidiophyceae under mixotrophic conditions is that it makes it possible to produce pure-strain (or axenic) cultures containing only one cell type inoculated in sterile culture medium, thus avoiding the problems of contamination by toxic strains as can be observed for raceway or open-pond cultures of *Spirulina platensis*. Apart from higher biomass productivity and/or biomass concentration, the fermenter culture method also offers more guarantees in terms of health safety.

The first object of the invention is thus a method for culturing unicellular red algae (URA) of the class Cyanidiophyceae, advantageously of the order Cyanidiales, more advantageously of the family Cyanidiaceae or Galdieriaceae, particularly of the genus *Cyanidioschyzon, Cyanidium* or *Galdieria*, more particularly of the species *Cyanidioschyzon merolae* 10D, *Cyanidioschyzon merolae* DBV201, *Cyanidium caldarium, Cyanidium daedalum, Cyanidium maximum, Cyanidium partitum, Cyanidium rumpens, Galdieria daedala, Galdieria maxima, Galdieria partita* or *Galdieria sulphuraria*, preferentially of the to species *Galdieria sulphuraria*, using a medium comprising at least one carbon source, and at least one phosphorus source, said method comprising at least one illumination step.

Such culture conditions can make it possible to achieve a higher URA biomass productivity and/or biomass concentration than the biomass productivity and/or biomass concentration obtained in the cultures of the prior art, can make it possible to obtain a larger amount of said biomass than the amount of biomass obtained in the cultures of the prior art and can promote protein production by said biomass which can reach up to 51% of the dry weight or more.

According to the invention, the illumination step of the method can be performed using white light or, advantageously, blue light. Indeed, the Applicant has demonstrated the fact that culturing URA, within the meaning of the invention, in blue light promotes phycocyanin production relative to the same culture but in white light. Therefore, according to a variant of the invention, the illumination step of the method can be performed using blue light.

According to the invention, by blue light is meant radiation having a narrow wavelength spectrum between 400 and 550 nm, preferentially between 420 nm and 500 nm. Such radiation can make it possible to obtain biomass rich in phycocyanin and in antioxidants, particularly carotenoids. According to a variant of the invention, said spectrum can be centred at 455 nm and not extend beyond 25 nm on each side. Preferably according to the invention, the selected wavelength will be between 430 and 480 nm, more preferentially the selected wavelength will be 455 nm.

According to the invention, the illumination can be produced by any means known to those skilled in the art, notably one or more lamps, one or more tubes, one or more light-emitting diodes (LEDs).

The Applicant has shown that the method is even more effective when the illumination is produced by one or more light-emitting diodes (LEDs).

Thus, according to a variant of the invention, the illumination can be produced by one or more LEDs. The LEDs are preferably commercially available LEDs.

By way of example, mention may be made of LEDs from Seoul Optodevice Co., LTD (South Korea), from Nichia Corporation (Japan), or from SunLED Corporation (USA).

According to the method of the invention, the culture can be subjected to light radiation for a sufficient period corresponding at least to the period necessary to meet the desired criteria of growth rate, phycocyanin level and/or carotenoid level. Those skilled in the art will be able, without excessive experimentation, to judge this required period. They will be able to adapt this time based on their knowledge of the field.

More particularly, mixotrophic conditions can be obtained under illumination conditions that are discontinuous and/or variable over time.

Discontinuous illumination refers to illumination punctuated by periods of darkness. The illumination can in particular be in the form of flashes. A flash, within the meaning of the invention, is light illumination of given duration.

According to the invention, three illumination concepts must be considered: the frequency or the number of flashes per unit of time, the duration of the flash, and the intensity of the light emitted.

In terms of frequency, according to the invention, according to the number of flashes per unit of time used in the method according to the invention, two types of illumination are defined:

a low-frequency illumination wherein the number of flashes can be between about 2 and $3.6 \cdot 10^4$ per hour ($5.4 \cdot 10^{-4}$ Hz to 10 Hz), preferably between 3 and $3.6 \cdot 10^3$ per hour ($8.3 \cdot 10^{-4}$ Hz to 1 Hz). It is understood here that the number of flashes per hour may have all the values between 2 and 36000 without it being necessary to mention them all (2, 3, 4, ..., 35598, 35599, 36000);
 a high-frequency illumination wherein the number of flashes can be between about $3.6 \times 10^4$ and $5.4 \times 10^9$ (10

Hz to $1.5 \cdot 10^6$ Hz) per hour, preferentially between $3.6 \times 10^5$ and $5.4 \times 10^9$ (100 Hz to $1.5 \cdot 10^6$ Hz). It is understood here that the number of flashes per hour may have all the values between $3.6 \times 10^6$ and $5.4 \times 10^6$ without it being necessary to mention them all (36000, 36001, 36002, . . . , 5399999998, 5399999999, 5400000000).

In terms of duration according to the invention, irrespective of the chosen illumination frequency, the flash duration can be between $\frac{1}{150000}$ of a second and 1799 seconds (29 minutes and 59 seconds).

Of course, when high-frequency illumination is used, the flash duration can be preferentially between $\frac{1}{150000}$ of a second and $\frac{1}{10}$ of a second.

And when low-frequency illumination is used, the flash duration can be preferentially between $\frac{1}{10}$ of a second and 1799 seconds (29 minutes and 59 seconds).

In terms of light intensity according to the invention, the intensity of the light provided in the form of flashes can be between 5 and 5000 $\mu mol \cdot m^{-2} \cdot s^{-1}$, preferably between 5 and 500 $\mu mol \cdot m^{-2} \cdot s^{-1}$, or 50 and 400 $\mu mol \cdot m^{-2} \cdot s^{-1}$, and more preferentially between 150 and 300 $\mu mol \cdot m^{-2} \cdot s^{-1}$ (1 $\mu mol \cdot m^{-2} \cdot s^{-1}$ corresponds to 1 $\mu E \ m^{-2} \cdot s^{-1}$ (einstein), a unit often used in the literature).

According to the invention, the number of flashes per hour can be selected as a function of the intensity and the duration of the flashes (see above).

According to the invention, the concepts of frequency, duration and light intensity apply to the illumination as envisaged by the invention, i.e., the illumination produced by the chosen light source, advantageously by an LED, emitting light radiation having a narrow spectrum between 400 and 550 nm, preferably 420 and 500 nm, even more preferentially between 430 and 480 nm, more preferentially centred at 455 nm and for the periods considered according to the invention.

A preferred form of the invention can be a method according to the invention in which the illumination can be provided in the form of discontinuous light in the form of flashes, obtained with LEDs emitting radiation having a narrow wavelength spectrum between 400 nm and 550 nm, preferentially between 420 nm and 500 nm, more preferentially between 430 and 480 nm, most preferentially a wavelength of 455 nm.

According to another embodiment of the invention, the illumination can be variable, which means that the illumination is not interrupted by phases of darkness, but that the light intensity varies over time. This variation of light intensity of can be regular or irregular and can be periodic or cyclic. According to the invention, light may also be provided in a combination of continuous and discontinuous illumination phases.

By variable illumination is meant that the light intensity varies in a regular manner at least twice per hour. An example of the illumination conditions suited to the method of the invention is described in application WO 2012/035262.

The illumination may have, preferably, variations of intensity the amplitude of which generally is between 5 $\mu mol \cdot m^{-2} \cdot s^{-1}$ and 2000 $\mu mol \cdot m^{-2} \cdot s^{-1}$, preferably between 50 and 1500 $\mu mol \cdot m^{-2} \cdot s^{-1}$, more preferentially between 50 and 200 $\mu mol \cdot m^{-2} \cdot s^{-1}$.

According to a preferred embodiment, the illumination has variations of intensity the amplitude of which is between 5 and 1000 $\mu mol \cdot m^{-2} \cdot s^{-1}$, preferably between 5 and 400 $\mu mol \cdot m^{-2} \cdot s^{-1}$, these variations taking place between 2 and 3600 times per hour, preferably between 2 and 200 times per hour.

These culture conditions make it possible to provide a defined quantity of light. This light provision may comprise discontinuous and/or variable illumination phases, with variations of intensity that may have identical or different amplitudes.

According to the invention, the culture conditions for the URA strains can be the conditions known and used in the prior art to cultivate the selected strains, conditions to which an illumination step has been added. Advantageously, the conditions which will make it possible to obtain the best biomass productivity and/or the best biomass concentration will be used.

Those skilled in the art will be able to integrate the illumination step according to the invention in a known method, for biomass that meets the desired criteria according to the invention in terms of growth rate and levels of metabolites of interest, particularly in levels of carotenoids and/or phycobiliproteins. In this respect, mention may be made of the methods described by Wolfgang Gross and Claus Schnarrenberger (op. cit.).

The methods for obtaining high biomass productivity or biomass concentration can be favoured. As an exemplary method, mention may be made of that described for example by Graverholt et al., [Appl. Microbiol. Biotechnol. (2007) 77:69-75].

More particularly, this step can be integrated in the methods described by the Applicant in application WO2012/035262.

According to the invention, the culture can be carried out by any known culture technique, for example in flasks or in a reactor, but also in a fermenters or in any container suited to URA growth such as, for example, raceways or open ponds, provided that said technique makes it possible to contact the URA with at least the carbon source, and moreover is equipped with at least one light source emitting in the wavelengths having a narrow spectrum between 400 nm and 550 nm, preferably between 430 and 480 nm, more preferentially centred at 455 nm, the action of which on the culture will be able to lead to the desired macroscopic composition of biomass, i.e., biomass rich in phycobiliproteins (phycocyanin and allophycocyanin) with intracellular concentrations between 29 and 250 mg/g of dry weight, preferentially between 35 and 150 mg/g of dry weight and optionally rich in antioxidants, in particular in carotenoids, advantageously zeaxanthin and β-carotene, in concentrations between 0.1 and 10 mg/g, advantageously between 0.250 and 1 mg/g.

These results in terms of dry biomass productivity and/or dry biomass concentration and of intracellular phycobiliprotein and carotenoid content can also be attained in $1 \text{-m}^3$, $4 \text{-m}^3$, $10 \text{-m}^3$ and $200 \text{-m}^3$ bioreactors, which are the volumes commonly used in industrial production.

The Applicant was also able to show that in the case of batch culture when the carbon (C) and phosphorus (P) concentrations in the initial culture medium are such that the P/C ratio of said concentrations (expressed in moles of phosphorus/moles of carbon) is lower than 0.01898, advantageously lower than 0.01503, more advantageously lower than 0.01054, even more advantageously lower than 0.00527, preferentially lower than 0.00263, most preferentially lower than 0.00131, then the intracellular phycocyanin content of the biomass is increased in relation to the intracellular phycocyanin content of biomass obtained under the standard conditions of the prior art.

Similarly, in fed-batch or continuous culture, the Applicant was able to show that when the amounts of phosphorus and carbon consumed are such that the P/C ratio of these consumed amounts (expressed in moles of phosphorus/moles of carbon) is lower than 0.01898, advantageously lower than 0.01503, more advantageously lower than 0.01054, even more advantageously lower than 0.00527, preferentially lower than 0.002637, more preferentially lower than 0.00131, then the phycocyanin content of the biomass is increased.

According to the invention, the phosphorus sources can be selected from the following: phosphoric acid, phosphorus salts, advantageously sodium hydrogen phosphate ($Na_2HPO_4$), or sodium dihydrogen phosphate ($NaH_2PO_4$), or potassium dihydrogen phosphate ($KH_2PO_4$), or potassium hydrogen phosphate ($K_2HPO_4$), or any mixture in any proportion of at least two of these sources.

According to the invention, the carbon sources can be selected from the following: glucose, glycerol, acetate, sucrose, or any mixture in any proportion of at least two of these sources.

Therefore, another object of the invention is a method for culturing URA of the class Cyanidiophyceae, advantageously of the order Cyanidiales, more advantageously of the family Cyanidiaceae or Galdieriaceae, particularly of the genus *Cyanidioschyzon, Cyanidium* or *Galdieria*, more particularly of the species *Cyanidioschyzon merolae* 10D, *Cyanidioschyzon merolae* DBV201, *Cyanidium caldarium, Cyanidium daedalum, Cyanidium maximum, Cyanidium partitum, Cyanidium rum pens, Galdieria daedala, Galdieria maxima, Galdieria partita* or *Galdieria sulphuraria*, preferentially of the species *Galdieria sulphuraria*, in a medium comprising at least one carbon source, and at least one phosphorus source, said method comprising at least one illumination step.

According to a first variant of the method according to the invention, in the case of batch culture, the carbon and phosphorus concentrations in the initial culture medium can be such that the P/C ratio of said concentrations (expressed in moles of phosphorus/moles of carbon) can be lower than 0.01898, advantageously lower than 0.01503, more advantageously lower than 0.01054, even more advantageously lower than 0.00527, preferentially lower than 0.00263, more preferentially lower than 0.00131.

According to a second variant of the method according to the invention, in the case of fed-batch or continuous culture, the amounts of carbon and phosphorus consumed during the culture can be such that the P/C ratio of these consumed amounts (expressed in moles of phosphorus/moles of carbon) can be lower than 0.01898, advantageously lower than 0.01503, more advantageously lower than 0.01054, even more advantageously lower than 0.00527, preferentially lower than 0.00263, more preferentially lower than 0.00131.

According to preferred variants of the method according to the invention, the latter can be carried out according to the variants described above but further comprising at least one illumination step performed using blue light.

Therefore, according to still another preferred variant of the method according to the invention, in the case of batch culture, said method comprising at least one illumination step performed using blue light, the carbon and phosphorus concentrations in the initial culture medium can be such that the P/C ratio of said concentrations (expressed in moles of phosphorus/moles of carbon) can be lower than 0.01898, advantageously lower than 0.01503, more advantageously lower than 0.01054, even more advantageously lower than 0.00527, preferentially lower than 0.00263, more preferentially lower than 0.00131.

And according to still another preferred variant of the method according to the invention, in the case of fed-batch or continuous culture, said method comprising at least one illumination step performed using blue light, the amounts of carbon and phosphorus consumed during the culture can be such that the P/C ratio of these consumed amounts (expressed in moles of phosphorus/moles of carbon) can be lower than 0.01898, advantageously lower than 0.01503, more advantageously lower than 0.01054, even more advantageously lower than 0.00527, preferentially lower than 0.00263, more preferentially lower than 0.00131.

According to these variants, the illumination conditions using blue light can be those described above.

Advantageously according to the invention, the method can comprise, simultaneously or independently, any other step necessary for growth of the biomass or for production of the molecules of interest (phycocyanin and carotenoids) such as, for example, without being limiting, one or more culture step(s) without light or one or more biomass collection step(s).

Generally according to the invention, the culture according to the method may be carried out at a temperature between 15° C. and 47° C., advantageously between 22° C. and 42° C.

According to the invention, the culture method can be used to cultivate a single URA strain of a given genus, several strains of a single given genus, or several strains of different given genera (at least two species of two different genera).

According to the invention, the carbon source can be selected from any known and usable carbon source according to the chosen strain. Those skilled in the art will easily know how to choose the carbon source best suited to the strain to be cultivated. By way of example, usable carbon sources include, but are not limited to, glucose, sucrose, acetate or glycerol [Wolfgang Gross and Claus Schnarrenberger, op. cit.].

The organic carbon substrate contained in the culture medium may consist of complex to molecules or a mixture of substrates. Products derived from the biotransformation of starch, for example from maize, wheat or potato, notably starch hydrolysates, which consist of small molecules, constitute, for example, organic carbon substrates suited to mixotrophic culture of the cells according to the invention.

The amounts of carbon sources used according to the method will of course depend on the chosen strain. Here again, those skilled in the art will easily know how to adapt the amounts of carbon source to the strain to be cultivated in pure form or in mixture.

According to an embodiment of the invention, the organic carbon substrate may have a concentration between 5 mM and 1.5 M, preferably 50 mM and 800 mM.

The method according to the invention can further comprise a step of collecting the URA. Said collection of the URA can be performed by any technique enabling collection of the biomass, in particular gravimetric or low-pressure filtration methods, decantation methods, or even precipitation methods followed by gravimetric filtration.

The invention also relates to the biomass obtainable by any one of the variants of the method according to the invention.

According to the invention, said biomass can have a URA density of at least 20 g/L and up to about 200 g/L of dry weight, preferentially of at least 50 g/L of dry weight, more preferentially of at least 90 g/L of dry weight and up to about 150 g/L of dry weight.

According to the invention, said biomass can have an intracellular phycobiliprotein (phycocyanin and allophycocyanin) content with intracellular concentrations between 29 and 250 mg/g of dry weight, preferentially between 35 and 150 mg/g of dry weight.

Further according to the invention, said biomass can have an intracellular phycocyanin content between 29 and 200 mg/g of dry weight, preferentially between 40 and 100 mg/g of dry weight.

According to the invention, the phycobiliproteins, and particularly the phycocyanin, produced by said biomass can be extracted to be used, for example, in food or as dye. Extraction of phycobiliproteins, and particularly of phycocyanin, from said biomass can be performed according to any extraction technique known to those skilled in the art, such as, for example, that described by Moon et al., 2014 (Myounghoon, Sanjiv K Mishra, Chul Woong Kim, William I Suh, Min S Park, and Ji-Won Yang. "Isolation and characterization of thermostable phycocyanin from *Galdieria sulphuraria*" 31 (2014): 1-6) or by Jouen et al., 1999 (Jaouen, P., B. Lepine, N R. Rossignol, R. Royer, and F. Quemeneur. "Clarification and concentration with membrane technology of a phycocyanin solution extracted from *Spirulina platensis*." Biotechnology Techniques 13, no. 12 (December 1999): 877-81. doi: 10.1023/A: 1008980424219.) or in patent FR2789399A1.

The invention thus also relates to a method for preparing phycocyanins which comprises the following steps:
a) cultivating URA of the class Cyanidiophyceae in a culture medium comprising at least one carbon source with at least one illumination step in the form of radiation having a narrow wavelength spectrum between 400 and 550 nm, in order to obtain a fermentation must comprising said URA in the culture media, with a cell density of at least 20 g/L of dry weight, as defined above and below,
b) collecting the biomass obtained from the fermentation must,
c) collecting the phycocyanins from the biomass.

The phycocyanin obtainable from said biomass has notable different properties in relation to the phycocyanin obtainable by culture of another organism, particularly for example in relation to the phycocyanin obtainable by culture of *spirulina*.

Said phycocyanin obtainable from the biomass obtained according to the invention, particularly from a *Galdieria sulphuraria* biomass, can have a blue colouring that fades little or not at all in a solution the pH of which is between 2 and 8, preferentially between 3 and 7, more preferentially between 4 and 5.

Moreover, the phycocyanin obtainable from the biomass obtained according to the invention, particularly from a *Galdieria sulphuraria* biomass, can have the advantage of precipitating little or not at all at acidic pH, particularly at a pH between 2 and 4, unlike the phycocyanin obtainable from a *spirulina* biomass. This property makes the phycocyanin obtainable from the biomass obtained according to the invention, particularly from a *Galdieria sulphuraria* biomass, an excellent candidate for use in carbonated or uncarbonated acidic beverages.

Moreover, the phycocyanin obtainable from the biomass obtained according to the invention, particularly from a *Galdieria sulphuraria* biomass, can have an enhanced thermostability in relation to that of the phycocyanin extracted from *spirulina* for temperatures above 50° C. (Moon et al., 2014).

Lastly, the phycocyanin obtainable from the biomass obtained according to the invention, particularly from a *Galdieria sulphuraria* biomass, can have an enhanced ethanol resistance in relation to the *spirulina* phycocyanin.

According to the invention, "resistance of the phycocyanin" (to acidic pH, to temperature and/or to ethanol) means an absence of colour loss or a colour loss that is less than that described for the phycocyanin extracted from *Spirulina platensis*. Colour fading can be quantified with a spectrophotometer by comparing the absorbance of an aqueous solution to under standard temperature and pH conditions, as described by Moon (2014), then comparing these results with those obtained under conditions of high temperature, acidic or alkaline pH, and/or when ethanol is added to the solution, for example.

Therefore, the invention also relates to the phycocyanin obtainable according to the method of the invention, said phycocyanin which can be resistant to a temperature between 70° C. and 0° C., preferentially between 65° C. and 25° C., more preferentially between 60° C. and 50° C., and/or resistant to a pH between 8 and 2, preferentially between 3 and 7, more preferentially between 4 and 5, and/or resistant to an ethanol concentration between 50% and 1%, preferentially between 40% and 10%, more preferentially between 20 and 30%.

The invention also relates to the use of the phycocyanin obtainable according to the method of the invention, in food or animal feed, as food supplement, or as dye, particularly as edible dye.

The meal obtainable after extracting phycocyanin from the URA biomass obtainable by the method according to the invention can be used as a protein and carotenoid-rich food supplement in food or animal feed.

According to the invention, said biomass can have an intracellular carotenoid content between 0.1 and 10 mg/g of dry weight, advantageously between 0.250 and 1 mg/g of dry weight.

URA have a high potential for use in many fields, such as food or animal feed, cosmetics, medicine, for example.

According to the invention, said URA biomass obtainable according to the invention can be used after harvest either directly, optionally dried, or after processing. In particular, said biomass can be used in the form of flours included in food compositions or in the form of food supplements.

The URA biomass obtainable according to the invention can be processed into flour according to any method known to those skilled in the art. It can thus be envisaged, for example, that the URA can be separated from the culture medium, lysed and reduced to fine particles (average diameter of 10 microns), then dried.

The invention also relates to any use of the URA biomass obtainable according to the invention in any known field of use of URA, particularly food or animal feed, cosmetics, medicine.

The biomass obtained after culturing URA according to the method of the invention can make it possible to obtain in particular a flour that is rich in antioxidants, in particular in carotenoids (particularly zeaxanthin and β-carotenes) in amounts between 0.1 and 10 mg/g of dry weight, advantageously between 0.25 and 1 mg/g of dry weight, in particular including to zeaxanthin in an amount between 0.05 and 5 mg/g of dry weight, advantageously between 0.1 and 1 mg/g of dry weight, and/or β-carotene in an amount between 0.05 and 5 mg/g of dry weight, advantageously between 0.1 and 1 mg/g of dry weight, meeting a need in particular in the food industry by virtue of being more appetizing, having better taste, providing antioxidants in a large amount and being usable in food or animal feed.

The invention thus relates to a flour obtainable after processing of the URA biomass obtainable by the method according to the invention.

Irrespective of the form of use of the product obtainable by the method according to the invention (native or processed biomass), said product can be used pure or mixed with other ingredients traditionally used, particularly in food or in cosmetics.

The invention also relates to any product that may comprise at least the algae biomass obtainable according to the invention. The invention also relates to any product that may comprise at least the flour derived from the processing of the algae biomass obtainable according to the invention.

DESCRIPTION OF THE FIGURES

FIG. 2A shows the intracellular phycocyanin content expressed in mg/g of dry weight (DW) ( ) and the cell concentration of the biomass estimated by measurement of optical density at 800 nm ( ). The test was performed in white light and in blue light. The measurements were made at 180 h and 250 h.

FIG. 2B shows the amount of chlorophyll ( ), β-carotene ( ) and zeaxanthin ( ) in the same cultures, in white light and in blue light, at 180 h and 250 h.

FIGS. 3A and 3C represent growth of the strain as a function of time in the presence of 1 (-Δ-), 2 (-□-), 4 (-O-) and 8 (-♦-) g/L ammonium sulphate (FIG. 3A) or of 250 (-Δ-), 500 (-□-), 1000 (-O-) and 2000 (-♦-) mg $KH_2PO_4$ (FIG. 3C).

FIGS. 3B and 3D represent the intracellular phycocyanin content expressed in mg/g of dry weight in the strains of the cultures in the presence of 1 ( ), 2 ( ), 4 ( ) and 8 ( ) g/L $(NH_4)_2SO_4$, at 250 h (FIG. 3B) or of 250 ( ), 500 ( ), 1000 ( ) and 2000 ( ) mg phosphorous $KH_2PO_4$ (FIG. 3D).

FIG. 4A shows the intracellular phycocyanin content expressed in mg/g of dry weight obtained under the different conditions tested. FIG. 4B shows the intracellular chlorophyll ( ) β-carotene ( ) and zeaxanthin ( ) contents in the same cultures.

FIG. 5A shows the tracking of the growth of the *Galdieria sulphuraria* strain in a fermenter by measurement of absorbance at 800 nm, and by measurement of dry weight per litre of must.

FIG. 5B shows the intracellular phycocyanin content expressed in mg/g of dry weight (DW).

FIG. 6A shows that phycocyanin extracted from *Galdieria sulphuraria* has good pH resistance: less than 20% loss of pigmentation up to pH 2.75, the loss becoming greater up to pH 2.

FIG. 6B shows that phycocyanin extracted from *Galdieria sulphuraria* has good temperature resistance: more than 40% of the pigmentation remaining after 30 minutes at 70° C.

FIG. 6C shows that phycocyanin extracted from *Galdieria sulphuraria* has good ethanol resistance: 40% loss of pigmentation in 30% ethanol, about 70% in 50% ethanol.

EXAMPLES

Example 1: Optimization of Growth in a Fermenter

Materials and Methods
Strain: *Galdieria sulphuraria* (Also Called *Cyanidium caldarium*) UTEX #2919
Culture Medium Heterotrophy and mixotrophy: 30 g/L glycerol, 8 g/L $(NH_4)_2SO_4$, 1 g/L $KH_2PO_4$, 716 mg/L $MgSO_4$, 44 mg/L $CaCl_2$, 3 mL/L Fe-EDTA stock solution (6.9 g/L $FeSO_4$ and 9.3 g/L EDTA-$Na_2$) and 4 mL/L trace metal solution (3.09 g/L EDTA-$Na_2$; 0.080 g/L $CuSO_4$, $5H_2O$; 2.860 g/L $H_3BO_3$; 0.040 g/L $NaVO_3$, $4H_2O$; 1.820 g/L $MnCl_2$; 0.040 g/L $CoCl_2$, $6H_2O$; 0.220 g/L $ZnSO_4$, $7H_2O$; 0.017 g/L $Na_2SeO_3$; 0.030 g/L $(NH_4)_6Mo_7O_{24}$, $4H_2O$).
Culture Conditions:

The cultures are carried out in 1- to 2-L-useful-volume reactors with computer-controlled automated systems. Culture pH is controlled by adding base (14% ammonia solution (w$NH_3$/w)) and/or acid (4 N sulphuric acid solution). Culture temperature is set to 42° C. Agitation is provided by three impellers: one Rushton turbine with six straight blades positioned at the lower end of the agitator shaft above the sparger and two triple-bladed HTPG2 impellers placed on the agitator shaft. Dissolved oxygen pressure in the liquid phase is regulated in the medium throughout the culture by the rotational speed of the agitator shaft (250-1800 rpm) and the air and/or oxygen ventilation flow rate. The regulatory parameters, integrated into the computer-controlled automated system, make it possible to maintain a partial pressure of dissolved oxygen in the liquid phase between 5 and 30% of the air saturation value under identical conditions of temperature, pressure and medium composition. Culture time was between 50 and 300 hours.

In order to optimize growth of the URA strains, various trophic modes were tested:

Heterotrophy (-♦-): The glycerol substrate is provided in fed-batch mode. No light is provided.

Mixotrophy (-O-): The glycerol substrate is provided in fed-batch mode and light is provided.

Results

The performance characteristics at the end of growth under the various conditions are summarized in Table 1 below.

TABLE 1

|  | Mixotrophy | Heterotrophy |
| --- | --- | --- |
| Time (h) | 100 | 350 |
| Cell concentration (g of dry biomass/L) | 98 | 68 |
| Yield (g/g of carbon substrate) | 0.5 | 0.5 |
| Productivity (g of dry biomass/L/h) | 0.98 | 0.19 |

Mixotrophic culture makes it possible to more quickly obtain a higher biomass concentration than those obtained with cultures in heterotrophic or autotrophic mode.

Biomass productivity in mixotrophic mode is 0.98 g of biomass/L/h, versus 0.19 g of biomass/L/h in heterotrophic mode. It is noted that in the prior art Graverholt et al. obtained productivity of 0.286 g/L/h in heterotrophic mode [Graverholt et al., op. cit.].

Figure 1:
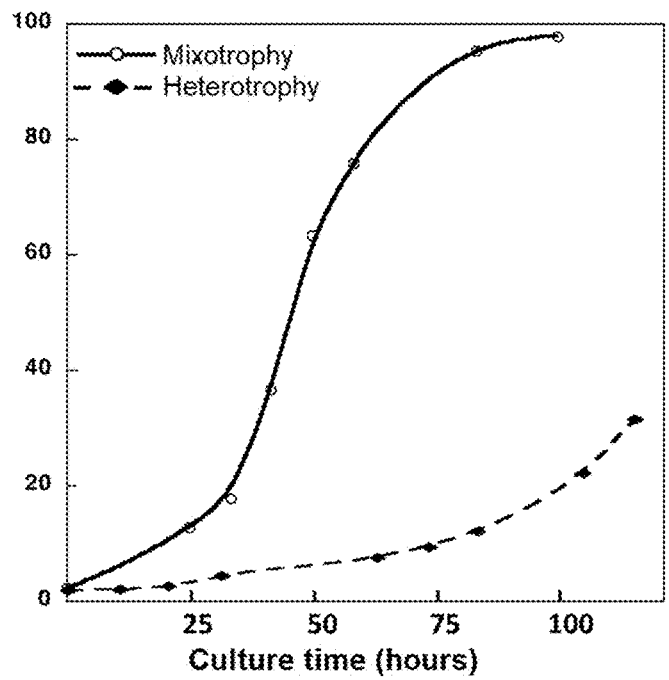
FIG. 1 describes the optimization of *Galdieria sulphuraria* growth in a bioreactor. It shows changes in biomass concentration as a function of time of a *Galdieria sulphuraria* strain according to the trophic mode of the culture used. The results show that mixotrophic conditions (-O-) make it possible to obtain faster and distinctly enhanced growth of the strain in relation to heterotrophic conditions (-♦-). This curve also shows that the dry biomass concentration is distinctly higher at the end of the culture with mixotrophic conditions than with heterotrophic conditions.

The results are presented in FIG. 1.

In addition to faster growth, the presence of light promotes protein production in the cells, which can reach 51.56% of the dry weight in mixotrophic mode versus 29.57% in heterotrophic mode (Table 2: Analyses of amino acid content of *G. sulphuraria* or *S. platensis* biomass).

TABLE 2

| A |  |  |  | Amino acids |  |  |  |  |  |
| --- | --- | --- | --- | --- | --- | --- | --- | --- | --- |
| *Galdieria sulphuraria* | ASP | GLU | ALA | ARG | CYS | GLY | HIS | ILE | LEU |
| % | 4.92 | 8.78 | 2.96 | 3.01 | 0.76 | 2.46 | 1.13 | 2.76 | 3.86 |
|  | LYS | MET | PHE | PRO | SER | THR | TYR | VAL | TOTAL |
| % | 3.81 | 1.20 | 2.25 | 2.96 | 3.60 | 3.44 | 0.00 | 3.66 | 51.56 |
| B |  |  |  | Amino acids |  |  |  |  |  |
| *Galdieria sulphuraria* | ASP | GLU | ALA | ARG | CYS | GLY | HIS | ILE | LEU |
| % | 2.99 | 5.34 | 1.62 | 1.57 | 0.46 | 1.33 | 0.62 | 1.41 | 2.07 |
|  | LYS | MET | PHE | PRO | SER | THR | TYR | VAL | TOTAL |
| % | 2.14 | 0.62 | 1.26 | 1.77 | 2.24 | 2.03 | 0.00 | 2.10 | 29.57 |
| C |  |  |  | Amino acids |  |  |  |  |  |
| *Spirulina platensis* | ASP | GLU | ALA | ARG | CYS | GLY | HIS | ILE | LEU |
| % | 6.11 | 8.77 | 4.85 | 4.14 | 0.62 | 3.20 | 1.05 | 3.53 | 5.42 |
|  | LYS | MET | PHE | PRO | SER | THR | TYR | VAL | TOTAL |
| % | 2.86 | 1.35 | 2.82 | 2.20 | 2.58 | 3.23 | 0.00 | 3.98 | 56.71 |

A) and B): Amino acid content of *Galdieria sulphuraria* cultivated under mixotrophic (A) and heterotrophic (B) conditions. The protein content estimated by the Kjeldahl method was estimated at 51.5% and 37% respectively with a factor N-6.25x.
C): Amino acid content of a commercial *Spirulina platensis* sample. The protein content estimated by the Kjeldahl method was estimated at 65% with a factor N-6.25x.

The high protein content of *Galdieria sulphuraria* makes it a good candidate to be included in the preparation of food supplements and thus to compete with *spirulina* in that market because its amino acid score is higher than that recommended by the FAO and its scores are higher than those of *spirulina* for four of the seven amino acids essential for human nutrition (Table. 3):

TABLE 3

Amino acid scores comparing FAO recommended daily requirements and the amounts provided by the strains of this study (mg/g of proteins) (adapted from FAO food and nutrition recommendation 92).

|  | His | Ile | Leu | Lys | Thr | Val | SSA |
| --- | --- | --- | --- | --- | --- | --- | --- |
| FAO recommendations | 16 | 30 | 61 | 48 | 25 | 40 | 23 |
| *Galdieria sulphuraria* | 21.94 | 53.59 | 74.95 | 73.98 | 66.80 | 71.07 | 38.06 |
| *Spirulina platensis* | 16.15 | 54.31 | 83.38 | 44.00 | 49.69 | 61.23 | 30.31 |

Example 2: Effect of Blue Light on Phycocyanin Production in Erlenmeyer Flasks on Strain *Galdieria sulphuraria*

Materials and Methods

Strain: *Galdieria sulphuraria* (or *Cyanidium caldarium*) UTEX #2919

Culture Medium:

30 g/L glycerol, 8 g/L $(NH_4)_2SO_4$, 1 g/L $KH_2PO_4$, 716 mg/L $MgSO_4$, 44 mg/L $CaCl_2$, 3 mL/L Fe-EDTA stock solution (6.9 g/L $FeSO_4$ and 9.3 g/L EDTA-$Na_2$) and 4 mL/L trace metal solution (3.09 g/L EDTA-$Na_2$; 0.080 g/L $CuSO_4$, $5H_2O$; 2.860 g/L $H_3BO_3$; 0.040 g/L $NaVO_3$, $4H_2O$; 1.820 g/L $MnCl_2$; 0.040 g/L $CoCl_2$, $6H_2O$; 0.220 g/L $ZnSO_4$, $7H_2O$; 0.017 g/L $Na_2SeO_3$; 0.030 g/L $(NH_4)_6Mo_7O_{24}$, $4H_2O$).

Culture Conditions;

In each 100-mL Erlenmeyer flask, medium is inoculated (0.1%, v/v) with a 240-hour-old preculture. To test the effect of light combined with phosphorus concentration, the Erlenmeyer flasks are independently illuminated with a system of white LEDs or blue LEDs (455 nm). The light intensity for each condition is 100 µmol m$^{-2}$ s$^{-1}$. The cells are cultivated at a temperature of 42° C. under moderate agitation (200 rpm). Tracking of cell growth is performed every 24 h by measurement of absorbance at 800 nm. When the stationary phase is reached (about 190 h), 50 mL of cell suspension is taken in order to perform a measurement of dry weight by filtration and measurements of phosphorus concentration in the medium by Reflectoquant® (methods known to those skilled in the art).

The estimation of intracellular phycocyanin content per gram of dry weight was performed at various culture times using the method described by Moon et al. [Moon et al., Korean J. Chem. Eng., 2014, 1-6] (A). The other pigments such as chlorophyll and carotenoids were estimated by an HPLC assay method known to those skilled in the art (B).
Results This test shows that already at 180 h the phycocyanin concentration is 300% higher in blue light than in white light (FIG. 2A). At 250 h this difference, although significant, is not more than 25%.

By analysing the phosphorus content of the medium at 250 h, it is noted that about 100 mg/L remains for the Erlenmeyer flasks in blue light, whereas in white light 5 mg/L remains, and that this is below the phosphorus values of the medium which induce phycocyanin to production, as will be seen later in point 3. At 180 h the strains do not contain chlorophyll but already β-carotene and zeaxanthin (FIG. 2B).

Tests with 475-nm wavelengths of blue light show an effect similar to that of 455 nm; it can thus be envisaged to use the entire blue light wavelength range to promote phycocyanin production.

Apart from white light, only blue light made it possible to obtain growth of the strain with phycocyanin production.

Figure 2:
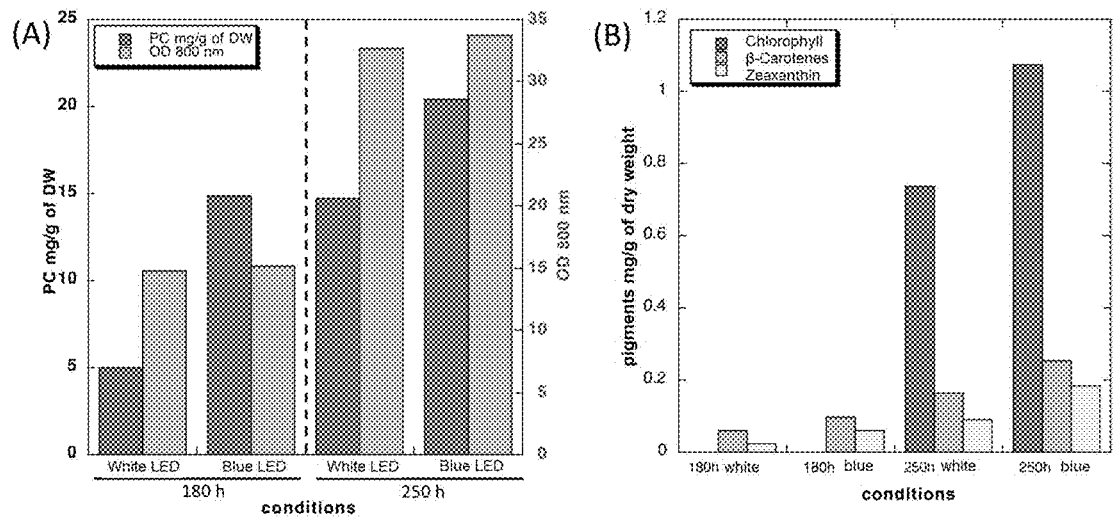
FIG. 2 shows the effect of blue light on growth and pigment production.

Exposure to blue light enables growth that is substantially equivalent to that observed in white light, with a significant increase in intracellular PC content per gram of dry weight (FIG. 2).

Example 3: Effect of Culture Medium Composition on Phycocyanin Production

Materials and Methods
Strain: *Galdieria sulphuraria* (Also Called *Cyanidium caldarium*) UTEX #2919
Culture Medium:

To test the effect of phosphorus concentration, the cultures were tracked on four different media. These media are composed of the same base:

30 g/L glycerol, 8 g/L $(NH_4)_2SO_4$, 716 mg/L $MgSO_4$, 44 mg/L $CaCl_2$, 3 mL/L Fe-EDTA stock solution (6.9 g/L $FeSO_4$ and 9.3 g/L EDTA-$Na_2$) and 4 mL/L trace metal solution (3.09 g/L EDTA-$Na_2$; 0.080 g/L $CuSO_4$, $5H_2O$; 2.860 g/L $H_3BO_3$; 0.040 g/L $NaVO_3$, $4H_2O$; 1.820 g/L $MnCl_2$; 0.040 g/L $CoCl_2$, $6H_2O$; 0.220 g/L $ZnSO_4$, $7H_2O$; 0.017 g/L $Na_2SeO_3$; 0.030 g/L $(NH_4)_6Mo_7O_{24}$, $4H_2O$).

For the phosphorus limitation, $KH_2PO_4$ concentrations of 250 mg/L, 500 mg/L, 1 g/L, and 2 g/L are set. Once the media are assembled, the pH is adjusted to 3 with 36 N $H_2SO_4$ then they are sterilized. The same protocol is applied for the media or the nitrogen concentration varies, this time keeping the $KH_2PO_4$ concentration at an initial value of 1 g/L. Culture conditions;

In each 100-mL Erlenmeyer flask, medium is inoculated (0.1%) with a 240-hour-old preculture. The cells are cultivated at a temperature of 42° C. under moderate agitation (140 rpm) with constant illumination by fluorescent tube (Osram 865 Cool Daylight) at 100 µmol $m^{-2}$ $s^{-1}$. Tracking of cell growth is performed every 24 h by measurement of absorbance at 800 nm.

Figure 3:
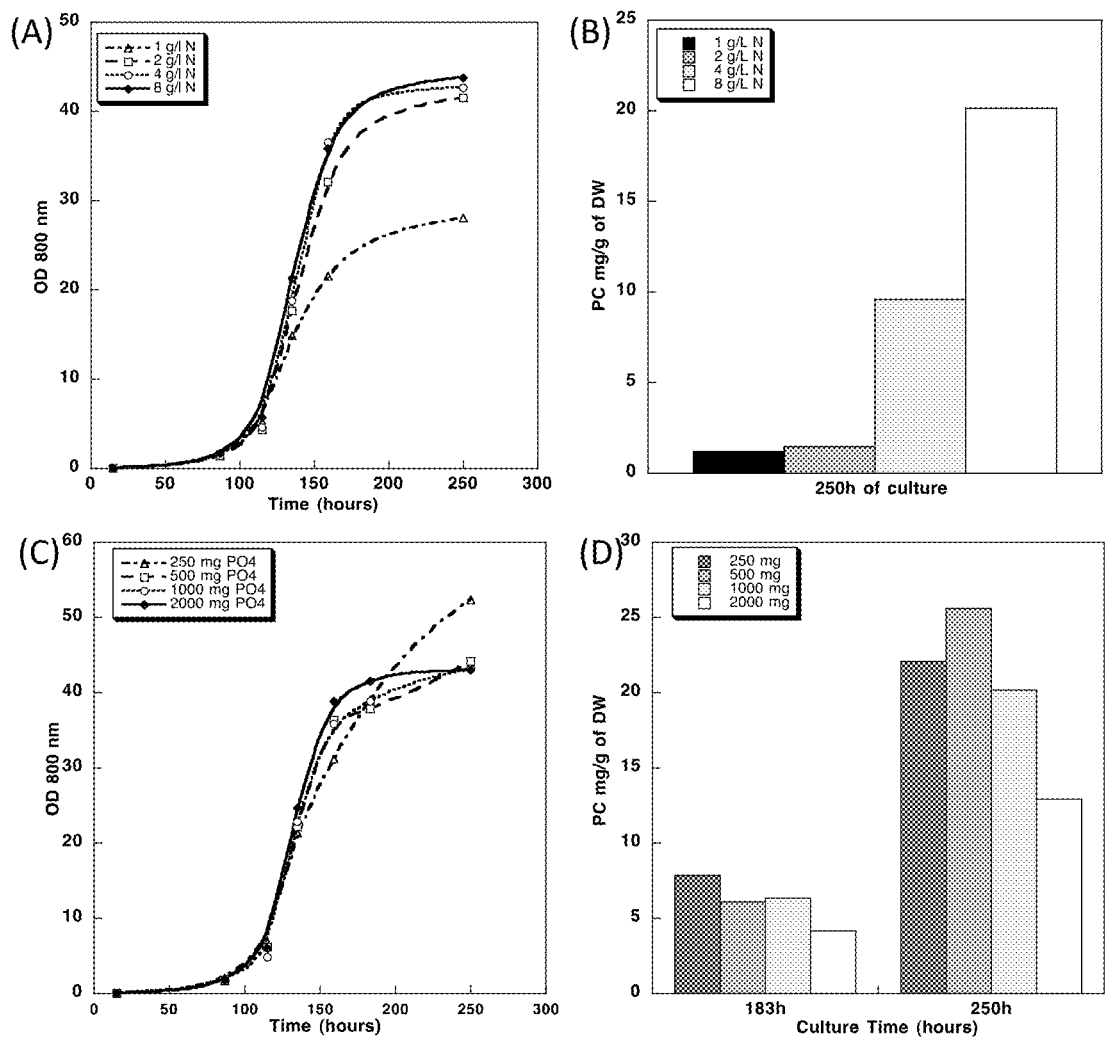
FIG. 3 shows the effect of nitrogen and phosphorus on growth and phycocyanin production. It shows the results obtained during the test of the influence of nitrogen concentration (FIGS. 3A and 3B) and of phosphorus concentration (FIGS. 3C and 3D) on *Galdieria sulphuraria* cultures.

The estimation of phycocyanin content per gram of dry weight was performed at various culture times using the method described by Moon et al. [Moon et al., Korean J. Chem. Eng., 2014, 1-6] (A). The other pigments such as chlorophyll and carotenoids were estimated by an HPLC assay method known to those skilled in the art (B).
Results:

FIG. 3 shows the results of these tests (A) Growth of the strain in the presence of various concentrations of $(NH_4)_2SO_4$ in the initial medium.

(B) Estimation of intracellular phycocyanin content in the biomass at the end of the culture;

(C) Growth of the strain in the presence of various concentrations of $KH_2PO_4$ in the initial medium;

(D) Estimation of the amount of PC in the biomass at 180 h and 250 h:

For these experiments, the cells are illuminated by white light (100 µE $m^{-2} \cdot s^{-1}$).

Save for adding large amounts of nitrogen to the culture medium aimed at promoting phycocyanin production, the Applicant was able to show that the amount of phosphorus in the medium is predominant for phycobiliprotein and carotenoid production (FIG. 3).

The Applicant was able to determine that for equivalent growths (FIG. 3C), i.e., for non-limiting phosphorus concentrations, phycocyanin production was higher in medium containing 250 mg/L $KH_2PO_4$ (or 0.0025 mole of phosphorus/L) than that obtained in medium containing 2 g/L $KH_2PO_4$ (or 0.2 mole of phosphorus/L) (FIG. 3B).

In a linear manner, the higher the phosphorus concentration in the initial medium for a fixed concentration of carbon source in the initial medium, the lower the intracellular phycocyanin content, and vice versa. In other words, the higher the P/C ratio of the initial concentrations in the medium (expressed in moles of phosphorus/moles of carbon), the higher the intracellular phycocyanin and carotenoid content in the biomass.

Consequently, the batch culture method aims at maintaining a phosphorus level in the medium which makes it possible to combine growth with phycobiliprotein and carotenoid production, by determining an ideal phosphorus concentration range. Contrary to what was described in international application WO2015107312 for *Chlorella*, phosphorus deficiency does not induce an overall increase in protein content in *Galdieria sulphuraria*. According to our results, the phycobiliprotein concentration increases whereas the protein content of the biomass (AA %) remains stable.

Example 4: Combined Effects of Blue Light and Phosphorus Concentration on Phycocyanin and Carotenoid Production Materials and Methods
Strain: *Galdieria sulphuraria* (or *Cyanidium caldarium*) UTEX #2919
Culture Medium:

30 g/L glycerol, 8 g/L $(NH_4)_2SO_4$, 716 mg/L $MgSO_4$, 44 mg/L $CaCl_2$, 3 mL/L Fe-EDTA stock solution (6.9 g/L $FeSO_4$ and 9.3 g/L EDTA-$Na_2$) and 4 mL/L trace metal solution (3.09 g/L EDTA-$Na_2$; 0.080 g/L $CuSO_4$, $5H_2O$; 2.860 g/L $H_3BO_3$; 0.040 g/L $NaVO_3$, $4H_2O$; 1.820 g/L $MnCl_2$; 0.040 g/L $CoCl_2$, $6H_2O$; 0.220 g/L $ZnSO_4$, $7H_2O$; 0.017 g/L $Na_2SeO_3$; 0.030 g/L $(NH_4)_6Mo_7O_{24}$, $4H_2O$).
Culture Conditions:

A range of concentrations of phosphorus, in the form of $KH_2PO_4$, in the presence of blue light or of white light, was used to grow *Galdieria sulphuraria* strains in Erlenmeyer flasks for 250 h.

| KH$_2$PO$_4$ | | | | | | | |
|---|---|---|---|---|---|---|---|
| 250 mg | 250 mg | 500 mg | 500 mg | 1000 mg Light | 1000 mg | 2000 mg | 2000 mg |
| White | Blue | White | Blue | White | Blue | White | Blue |
| Condition 1 | 2 | 3 | 4 | 5 | 6 | 7 | 8 |

In each 100-mL Erlenmeyer flask, medium is inoculated (0.1%, v/v) with a 240-hour-old preculture. To test the effect of light combined with phosphorus concentration, the Erlenmeyer flasks are independently illuminated with a system of white LEDs or blue LEDs (455 nm). The light intensity for each condition is 100 µmol m$^{-2}$ s$^{-1}$. The cells are cultivated at a temperature of 42° C. under moderate agitation (200 rpm). Tracking of cell growth is performed every 24 h by measurement of absorbance at 800 nm.

Figure 4:
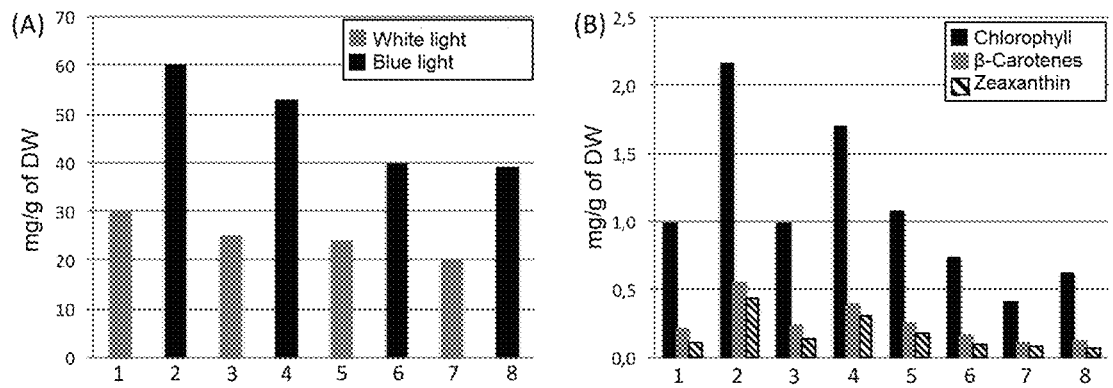
FIG. 4 shows the combined effects of blue light and of phosphorous limitation on pigment production on *Galdieria sulphuraria* cultures.

Results:

FIG. 4 shows the results of these tests

Visually, the strains have a difference in colouring ranging from blue-green, through green, to pale yellow.

Similar to what was described in the previous experiments, the positive effect of blue light and of phosphorus deficiency is found.

Cross-comparison of the data clearly shows that the most favourable condition for pigment production—whether phycocyanin, carotenoids or chlorophyll—is culture in blue light in the presence of low phosphorus concentration.

Table 4 below shows the concentrations of the various pigments in the biomass after 250 h of growth.

TABLE 4

Concentration of the various pigments in the biomass after 250 h of growth.

| Conditions | Phycocyanin* | Chlorophyll A* | β-Carotene* | Zeaxanthin* |
|---|---|---|---|---|
| 1 | 30 | 0.989 | 0.214 | 0.115 |
| 2 | 60 | 2.154 | 0.543 | 0.441 |
| 3 | 25 | 0.993 | 0.239 | 0.131 |
| 4 | 53 | 1.687 | 0.393 | 0.307 |
| 5 | 24 | 1.073 | 0.252 | 0.182 |
| 6 | 40 | 0.738 | 0.162 | 0.089 |
| 7 | 20 | 0.408 | 0.114 | 0.081 |
| 8 | 39 | 0.622 | 0.120 | 0.063 |

*(mg/g of dry weight)

Although significant in both cases, the effect of phosphorus concentration is much more marked in the presence of blue light than of white light, the concentrations which can be multiplied by 2 for phycocyanin (FIG. 4A and Table 4), by 4.5 for the β-carotenes, and by 7 for zeaxanthin (FIG. 4B and Table 4).

Example 5: Combined Effects of Blue Light and of Phosphorus Concentration on Phycocyanin and Carotenoid Production in Continuous Culture Culture Conditions:

Strain Galdieria UTEX 2919 was cultivated under the conditions of Example 1, with 500 mg of KH$_2$PO$_4$ and a blue baffle delivering up to 3 watts of light power at a wavelength of 455 nm. The feed medium is proportioned so as to obtain between 60 and 65 g of dry weight per litre of must. The concentration of each element of the medium is adjusted in order to respect the ratios of the medium used for the starter culture described in Example 1.

For the first culture phase corresponding to batch culture, fed-batch and then to stabilization around 60 g of DW/L, the light is maintained at 50% of the maximum power. After 600 hours of culture, regarded as the production phase, the light power was increased to 100%, or 3 watts.

Figure 5:
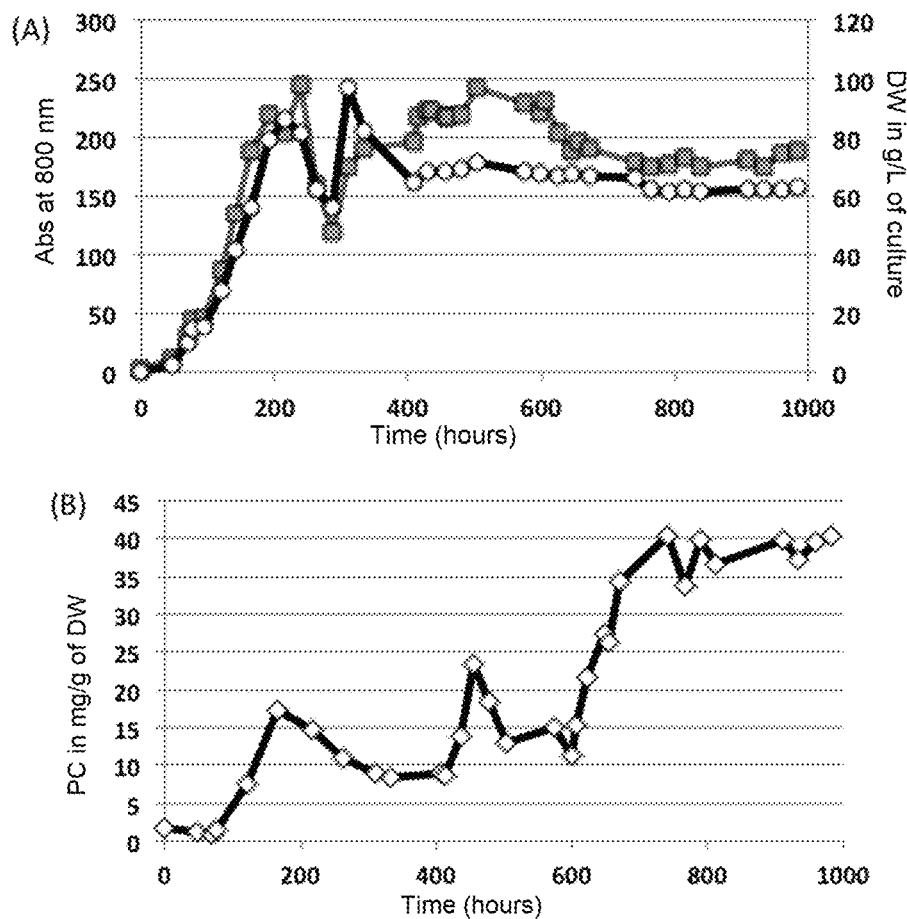
FIG. 5 shows the tracking of the culture in a fermenter in continuous mode with blue-light baffles (455 nm)

FIG. 5A: (-O-) tracking of growth by dry weight; (-□-) tracking of growth by measurement of absorbance at 800 nm.

FIG. 5B: Measurement of change in intracellular phycocyanin content during the culture.

Results:

After 3 weeks, the permanent culture regime was established between 60 and 65 g of DW per litre of must (FIG. 5A). When the light power is increased at 600 h, the result is a gradual increase in PC content in the biomass until 40 mg/g of DW is reached. On average, the PC content measured over the last 200 hours of culture remains close to that value.

Example 6: Physicochemical Characterization of Phycocyanin Extracted from Strain Galdieria UTEX 2919 Cultivated According to the Invention Test Protocols Strain Galdieria UTEX 2919 was cultivated under the conditions of Example 2.

For these tests, phycocyanin was extracted according to the protocol described by Moon et al., 2014 (op. cit.). The blue colour of the phycocyanin is measured by absorbance at 618 nm using a spectrophotometer (Amersham Biosciences Ultra Spec 2100 Pro). Percentage colour loss is calculated relative to the absorbance measurement of the sample under the reference conditions, pH 6 for the pH test, 25° C. for the temperature test, 0% ethanol for resistance to alcohol.

For the test of resistance to acidic conditions, the pH is gradually lowered by adding citric acid solution to the phycocyanin preparation. For each pH value, a sample of the phycocyanin solution is taken and its absorbance at 618 nm is measured.

For the tests of resistance to temperature, the phycocyanin solution is placed for 30 minutes in a water bath preheated to 70° C.; after cooling to room temperature the absorbance of the sample at 618 nm is measured.

For the tests of resistance to alcohol, 1 volume of phycocyanin solution is mixed with 1 equivalent volume of a 0%, 40%, 60%, 80% and 100% ethanol solution in order to produce a phycocyanin solution containing 0%, 20%, 30%, 40% and 50%, respectively. After 1 hour of incubation, a measurement of absorbance at 618 nm is made for each mixture.

Figure 6:
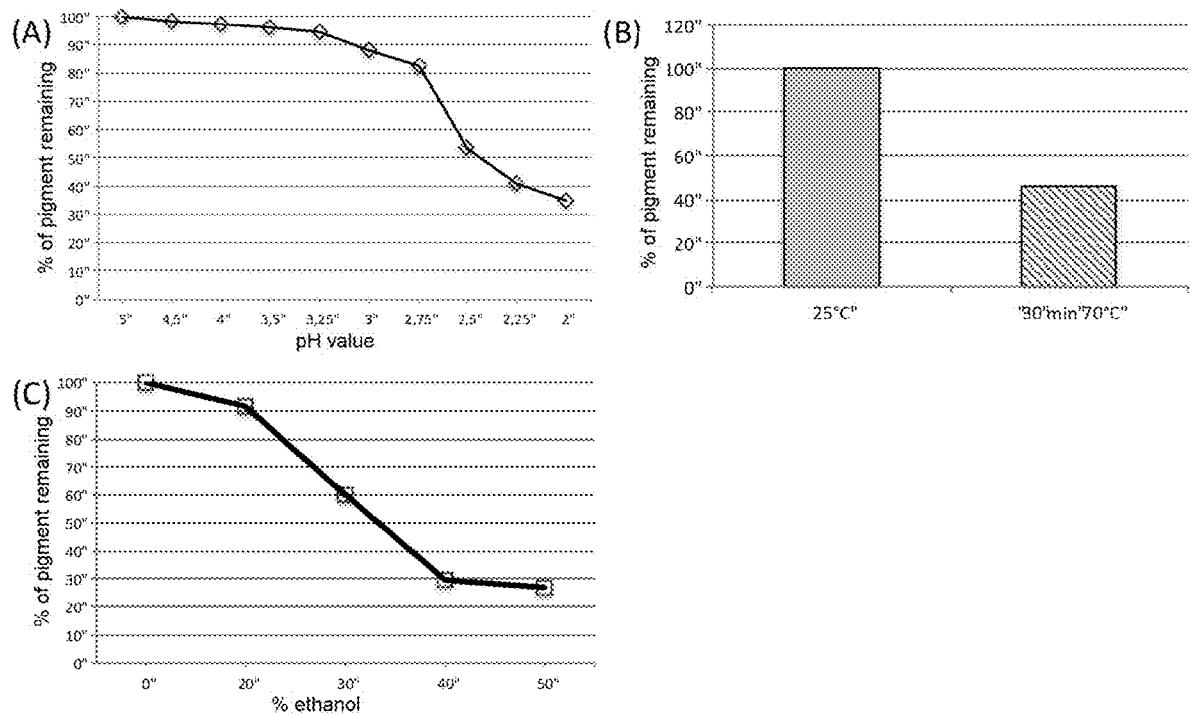
FIG. 6 shows the physicochemical characteristics of phycocyanin extracted from *Galdieria sulphuraria* compared with phycocyanin extracted from *Spirulina platensis*. (A) Test of pH resistance, (B) Temperature resistance. (C) Ethanol resistance.

Results:

The results of these tests are presented in FIG. 6

FIG. 6A shows that phycocyanin extracted from strain *Galdieria sulphuraria* (UTEX 2919) has more than 80% of its colouring at pH 2.75.

FIG. 6B shows that phycocyanin extracted from strain *Galdieria sulphuraria* (UTEX 2919) has more than 40% of its colouring after 30 minutes of incubation at 70° C.

FIG. 6C shows that phycocyanin extracted from strain *Galdieria sulphuraria* (UTEX 2919) has more than 30% of its colouring after 1 hour of incubation in 40% ethanol.

These results are comparable to those described in the prior art for *spirulina* phycocyanin (www.dlt-spl.co.jp/business/en/*spirulina*/linablue.htm).

REFERENCES

Chen, Feng, and Yiming Zhang; Enzyme and Microbial Technology 20, no. 3 (Feb. 15, 1997): 221-24
Sloth J K et al., ENZYME AND MICROBIAL TECHNOLOGY, Vol. 28, no. 1-2, January 2006, 168-175
Graverholt O S et al., APPLIED MICROBIOLOGY AND BIOTECHNOLOGY, Vol. 77, no. 1, 5 Sep. 2007, 69-75
Gross W and Schnarrenberger C, "Heterotrophic Growth of Two Strains of the Acido-to Thermophilic Red Alga *Galdieria sulphuraria*." Plant and Cell Physiology 36, no. 4 (Jun. 1, 1995): 633-38
Jouen et al., 1999, "Clarification and concentration with membrane technology of a phycocyanin solution extracted from *Spirulina platensis*." Biotechnology Techniques 13, no. 12 (December 1999): 877-81
Moon et al., 2014, "Isolation and characterization of thermostable phycocyanin from *Galdieria sulphuraria*" 31 (2014): 1-6)
Nichols K et al., BOTANICAL GAZETTE, Vol. 124, no. 2, 1 Dec. 1962, 85-93
Steinmuler K et al., PLANT PHYSIOLOGY, Vol. 76, no. 4, 1 Dec. 1984, 935-939
Rellan, S, et al.; Food and Chemical Toxicology 47 (2009) 2189-2195 FR 2 789 399
WO2012/035262

The invention claimed is:

1. A method for culturing unicellular red algae (URA) of the class Cyanidiophyceae, said method comprising:
illuminating a culture medium comprising the URA, a phosphorus source, and a carbon source for a period of time with a radiation having a wavelength spectrum between 400 and 550 nm, wherein the period of time is sufficient to obtain fermentation of said URA in the culture medium, with a cell density of at least 20 g/L of dry weight,
and wherein an initial carbon and phosphorus concentration of the culture medium in a batch culture, or an amount of carbon and phosphorus consumed in the culture medium during a fed-batch or continuous culture, expressed in moles of phosphorus/moles of carbon, is lower than 0.01898.

2. The method of claim 1, wherein the URA are of the order Cyanidiales.

3. The method of claim 1, wherein the wavelength spectrum is between 420 nm and 500 nm.

4. The method of claim 1, wherein the carbon source is selected from the group consisting of glucose, sucrose, acetate and glycerol.

5. The method of claim 1, wherein the carbon source is present in the culture medium at an initial concentration of between 5 mM and 1.5 M.

6. A method for culturing unicellular red algae (URA) of the class Cyanidiophyceae, said method comprising:
illuminating a culture medium comprising the URA, a phosphorus source and a carbon source for a period of time with a radiation having a wavelength spectrum between 400 and 550 nm, wherein the period of time is sufficient to obtain fermentation of said URA in the culture medium, with a cell density of between 20 and 200 g/L of dry weight,
and wherein an initial carbon and phosphorus concentration of the culture medium in a batch culture, or an amount of carbon and phosphorus consumed in the culture medium during a fed-batch or continuous culture, expressed in moles of phosphorus/moles of carbon, is lower than 0.01898.

7. A method for culturing unicellular red algae (URA) of the class Cyanidiophyceae, said method comprising:
illuminating a culture medium comprising the URA, a phosphorus source and a carbon source for a period of time with a radiation having a wavelength spectrum between 400 and 550 nm, wherein the period of time is sufficient to obtain fermentation of said URA in the culture medium, with a cell density of at least 20 g/L of dry weight, wherein the fermentation has a phycobiliprotein (phycocyanin and allophycocyanin) content between 29 and 250 mg/g of dry weight,
and wherein an initial carbon and phosphorus concentration of the culture medium in a batch culture, or an amount of carbon and phosphorus consumed in the culture medium during a fed-batch or continuous culture, expressed in moles of phosphorus/moles of carbon, is lower than 0.01898.

8. A method for culturing unicellular red algae (URA) of the class Cyanidiophyceae, said method comprising:
illuminating a culture medium comprising the URA, a phosphorus source and a carbon source for a period of time with a radiation having a wavelength spectrum between 400 and 550 nm, wherein the period of time is sufficient to obtain fermentation of said URA in the culture medium, with a cell density of at least 20 g/L of dry weight, wherein the fermentation has a phycocyanin content between 29 and 200 mg/g of dry weight,
and wherein an initial carbon and phosphorus concentration of the culture medium in a batch culture, or an amount of carbon and phosphorus consumed in the culture medium during a fed-batch or continuous culture, expressed in moles of phosphorus/moles of carbon, is lower than 0.01898.

9. The method of claim 6, wherein the URA are of the order Cyanidiales.

10. The method of claim 6, wherein the wavelength spectrum is between 420 nm and 500 nm.

11. The method of claim 6, wherein the carbon source is selected from the group consisting of glucose, sucrose, acetate and glycerol.

12. The method of claim 6, wherein the carbon source is present in the culture medium at an initial concentration of between 5 mM and 1.5 M.

13. The method of claim 12, wherein the URA are of the order Cyanidiales.

14. The method of claim 12, wherein the wavelength spectrum is between 420 nm and 500 nm.

15. The method of claim 12, wherein the carbon source is selected from the group consisting of glucose, sucrose, acetate and glycerol.

16. The method of claim 12, wherein the carbon source is present in the culture medium at an initial concentration of between 5 mM and 1.5 M.

17. The method of claim 8, wherein the URA are of the order Cyanidiales.

18. The method of claim 8, wherein the wavelength spectrum is between 420 nm and 500 nm.

19. The method of claim 8, wherein the carbon source is selected from the group consisting of glucose, sucrose, acetate and glycerol.

20. The method of claim 8, wherein the carbon source is present in the culture medium at an initial concentration of between 5 mM and 1.5 M.

\* \* \* \* \*